United States Patent
Henry

(10) Patent No.: US 9,566,408 B2
(45) Date of Patent: Feb. 14, 2017

(54) AIR DELIVERY CONDUIT

(75) Inventor: Robert Edward Henry, Roseville (AU)

(73) Assignee: ResMed Limited, Bella Vista (AU)

( * ) Notice: Subject to any disclaimer, the term of this patent is extended or adjusted under 35 U.S.C. 154(b) by 1210 days.

(21) Appl. No.: 12/225,417

(22) PCT Filed: Mar. 22, 2007

(86) PCT No.: PCT/AU2007/000358
§ 371 (c)(1),
(2), (4) Date: Jan. 29, 2009

(87) PCT Pub. No.: WO2007/109837
PCT Pub. Date: Oct. 4, 2007

(65) Prior Publication Data
US 2010/0224195 A1    Sep. 9, 2010

(30) Foreign Application Priority Data
Mar. 24, 2006 (AU) ................ 2006901506

(51) Int. Cl.
*A61M 16/00* (2006.01)
*A61M 16/14* (2006.01)
*A61M 16/08* (2006.01)

(52) U.S. Cl.
CPC ....... *A61M 16/142* (2014.02); *A61M 16/0875* (2013.01)

(58) Field of Classification Search
CPC A61M 16/142; A61M 16/0875; A61M 16/08; A61M 16/1095; A62B 9/003
USPC .......... 128/205.25, 204.18, 203.16, 205.12,128/205.27, 200.24, 911; 428/36.1; 138/118–139
See application file for complete search history.

(56) References Cited

U.S. PATENT DOCUMENTS

| 3,709,262 | A | * | 1/1973 | Braunschweiler .............. 139/14 |
| 4,437,462 | A | * | 3/1984 | Piljay et al. ............. 128/207.11 |
| 4,714,096 | A | * | 12/1987 | Guay ............................ 139/391 |
| 4,848,366 | A | * | 7/1989 | Aita et al. ..................... 128/863 |
| 5,418,051 | A | * | 5/1995 | Caldwell ......................... 442/61 |
| 5,548,842 | A | * | 8/1996 | Wiseman, Sr. ..................... 2/69 |
| 5,735,266 | A | * | 4/1998 | Smith ..................... 128/204.18 |
| 5,800,402 | A | * | 9/1998 | Bierman ...................... 604/180 |
| 5,843,542 | A | * | 12/1998 | Brushafer et al. ........... 428/36.1 |

(Continued)

FOREIGN PATENT DOCUMENTS

| BR | 8904121 | 4/1990 |
| CA | 1106101 | 8/1981 |

(Continued)

OTHER PUBLICATIONS

Timco Rubber, Aug. 22, 2014, Timco Rubber, http://www.timcorubber.com/rubber-materials/butyl.htm.*

(Continued)

*Primary Examiner* — Bradley Philips
(74) *Attorney, Agent, or Firm* — Nixon & Vanderhye P.C.

(57) ABSTRACT

An air delivery conduit for conveying breathable gas from a positive airway pressure device to a patient interface includes a tubular wall structure constructed from a textile material. A reinforcing structure may be provided to the wall structure that is structured to prevent kinking or collapsing of the wall structure. The wall structure may include a warp having a plurality of lengthwise textile warp threads arranged in a circle and a weft having a textile weft thread that is woven through the warp threads.

21 Claims, 2 Drawing Sheets

(56) References Cited

U.S. PATENT DOCUMENTS

| | | | |
|---|---|---|---|
| 6,769,431 B2* | 8/2004 | Smith et al. | 128/203.16 |
| 6,779,522 B2* | 8/2004 | Smith | A61M 16/08 |
| | | | 128/203.16 |
| 7,481,221 B2* | 1/2009 | Kullik et al. | 128/207.11 |
| 8,435,216 B2* | 5/2013 | Spinoza | 604/174 |
| 2002/0005197 A1* | 1/2002 | DeVries et al. | 128/204.21 |
| 2003/0070680 A1* | 4/2003 | Smith et al. | 128/204.17 |
| 2004/0211422 A1* | 10/2004 | Arcilla et al. | 128/204.19 |
| 2004/0226813 A1* | 11/2004 | Wang | 204/157.3 |
| 2008/0202512 A1* | 8/2008 | Kressierer / Huber et al. | 128/202.27 |
| 2008/0228028 A1* | 9/2008 | Carlson et al. | 600/36 |
| 2010/0255270 A1* | 10/2010 | Stuebiger | 428/201 |

FOREIGN PATENT DOCUMENTS

| | | | |
|---|---|---|---|
| EP | 393686 | 10/1990 | |
| EP | 430117 | 6/1991 | |
| GB | 656352 | 8/1951 | |
| JP | 9047159 | 2/1997 | |
| SU | 1682708 | 10/1991 | |
| WO | WO 9910250 A1 * | 3/1999 | B65D 63/12 |
| WO | WO 2006/047818 | 5/2006 | |

OTHER PUBLICATIONS

International Search Report of PCT/AU2007/000358, dated Apr. 30, 2007, 3 pgs.

* cited by examiner

AIR DELIVERY CONDUIT

CROSS REFERENCE TO RELATED APPLICATIONS

This application is the U.S. national phase of International Application No. PCT/AU2007/000358, filed Mar. 22, 2007, which designated the U.S. and claims the benefit of Australian Provisional Application No. AU2006901506, filed Mar. 24, 2006, each of which is incorporated herein by reference in its entirety.

FIELD OF THE INVENTION

The present invention relates generally to the field of respiratory therapy. More particularly, the invention relates to positive airway pressure devices (PAP devices), respirators, ventilators, CPAP or VPAP devices and conduits that form a component of such devices, the conduits being used for conveying breathing gas from the device to a patient interface.

BACKGROUND 1.0 Introduction

Respiratory devices typically include a flexible conduit to convey a breathing gas such as air to a patient. Generally, the conduit should be strong enough to prevent crushing or kinking, as such could cause occlusions in the conduit thereby restricting or blocking the delivery of breathing gas.

1.1 General Structure

One known conduit structure includes a hard plastic or metal spiral reinforcement around the inside or outside of a thin-walled flexible plastic tube. This helical or spiral structure supports the tube and prevents occlusions. Preferably, the spiral is wound around the outside of the plastic tube so that the conduit maintains a smooth bore, such as in Smooth-Bore tubing.

1.2 Heat Transfer

Humidified breathing gas may be delivered to a patient as part of their respiratory therapy. In this case, it is advantageous to minimise head transfer out of the conduit in order to avoid condensation of the humidified gas as it flows through the conduit. The condensation problem is particularly pronounced in cold environments.

Plastics and metals are not efficient thermal insulators. Therefore, in order to prevent condensation, additional structure may be added to the conduit. For example, an insulating sleeve may be used to cover the conduit and provide insulation. Another proposed solution involves using a heated wire to heat the conduit (Thermo-Smart® by Fisher & Paykel Healthcare). Actively heating the tube may result in the air temperature rising as it travels along the tube which in turn will result in the air drying out. Smooth-Bor™ also produces a dual-walled conduit that provides added insulation.

1.3 Weight

Present conduits can also be heavy causing an uncomfortable resistance to patient head movements. Additional items, such as an insulating sleeve, added to the conduit may cause the overall weight to increase. Additional items may also increase the friction of the conduit against surrounding items, such as bed linen.

SUMMARY OF THE INVENTION

A first aspect of the invention is to provide a conduit suitable to deliver air from a positive airway pressure device (PAP device), blower, flow generator or ventilator to a patient interface to provide respiratory therapy. In one form the conduit is at least partly constructed from a textile. In one form a wall of the conduit is at least partly constructed from a textile.

In one form, the wall is made from a non-porous, woven textile.

In one form, the textile is woven and porous but is treated such that it is substantially non-porous.

In one form, the textile is a woven textile, manufactured by a circular weaving manufacturing process. Advantageously, the resultant textile is tubular.

In one form, the conduit includes a reinforcing structure and a wall structure, and at least a portion of either the reinforcing structure or the wall structure includes a textile.

A second aspect of the invention is a method for manufacturing a wall of a conduit for conveying air from a respiratory device to a patient interface, the method comprising weaving a textile wall by a circular weaving technique.

Another aspect of the invention relates to an air delivery conduit for conveying breathable gas from a positive airway pressure device to a patient interface. The air delivery conduit includes a tubular wall structure constructed from a textile material and a reinforcing structure provided to the wall structure. The reinforcing structure is structured to prevent kinking or collapsing of the wall structure.

Another aspect of the invention relates to a method for manufacturing an air delivery conduit for conveying breathable gas from a positive airway pressure device to a patient interface. The method includes providing a warp having a plurality of lengthwise textile warp threads arranged in a circle, providing a weft having a textile weft thread, and weaving the weft thread through the plurality of warp threads in a circular weaving technique to produce a tubular wall structure.

Advantageously, textiles (including woven and non-woven textiles) usually provide better insulating properties than plastics and are often lighter in weight. A non-porous textile advantageously prevents breathing gas escaping from the conduit (and the resultant pressure losses).

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

2.1 Structure

Figure 1:
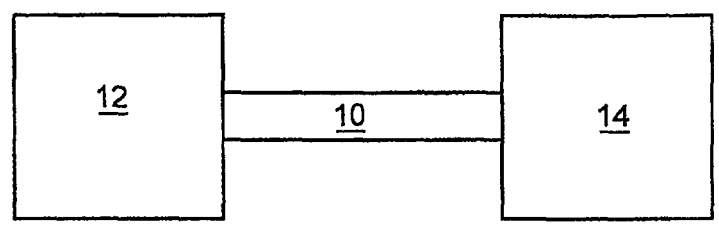
FIG. 1 is a schematic view of an air delivery conduit to deliver air from a PAP device to a patient interface according to an embodiment of the present invention.

As schematically shown in FIG. 1, an air delivery conduit 10 is provided that is suitable to deliver air from a positive airway pressure device (PAP device), blower, flow generator, or ventilator 12 to a patient interface 14 to provide respiratory therapy. In one form the conduit 10 is at least partly constructed from a textile.

Figure 2:
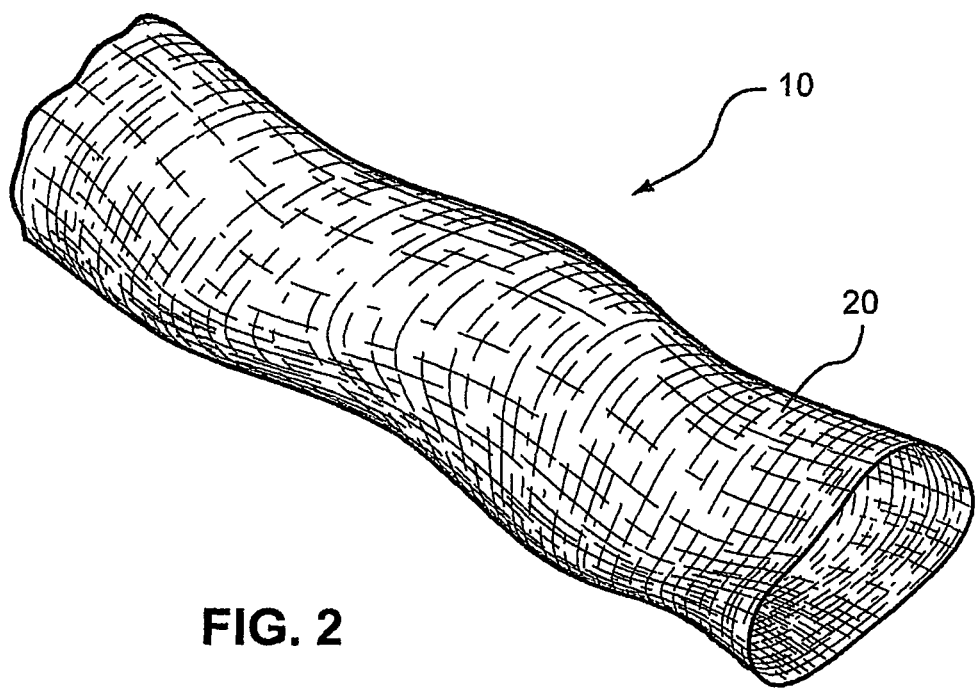
FIG. 2 is a perspective view of a textile conduit according to an embodiment of the present invention.

For example, FIG. 2 illustrates a conduit 10 according to an embodiment of the present invention. As illustrated, a wall or wall structure 20 of the conduit 10 is at least partly constructed from a textile. The conduit 20 may be provided with suitable end portions, e.g., plastic cuffs, that are structured to connect the conduit 10 to each of the PAP device 12 and the patient interface 14.

Figure 3:
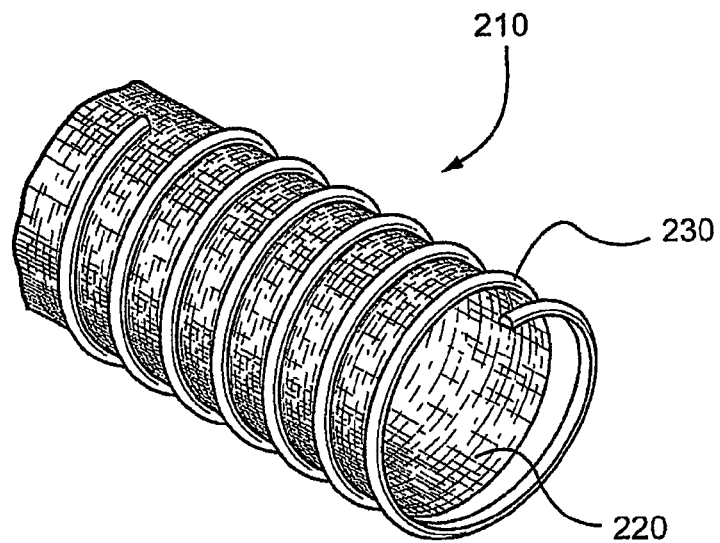
FIG. 3 is a perspective view of a textile conduit with a reinforcing structure according to an embodiment of the present invention.

In one form, the conduit includes a reinforcing structure and a wall structure, and at least a portion of either the reinforcing structure or the wall structure includes a textile. For example, FIG. 3 illustrates a conduit 210 according to another embodiment of the present invention. As illustrated, the conduit 210 includes a wall or wall structure 220 constructed from a textile and a reinforcing structure 230 provided to the wall 220.

In the illustrated embodiment, the reinforcing structure 230 is a spiral structure attached to the textile wall 220 so that the resulting conduit is strong enough to prevent kinking or collapsing. A plastic reinforcing structure 230 that has a spiral/helical shape or a webbing could be used.

2.1.1 Circular Weaving

In an embodiment, the textile is a woven textile, manufactured by a circular weaving manufacturing process. The resultant textile is tubular. In circularly weaved conduits, the warp is circular and there are continuously circulating shuttles running around the periphery.

Figure 4:
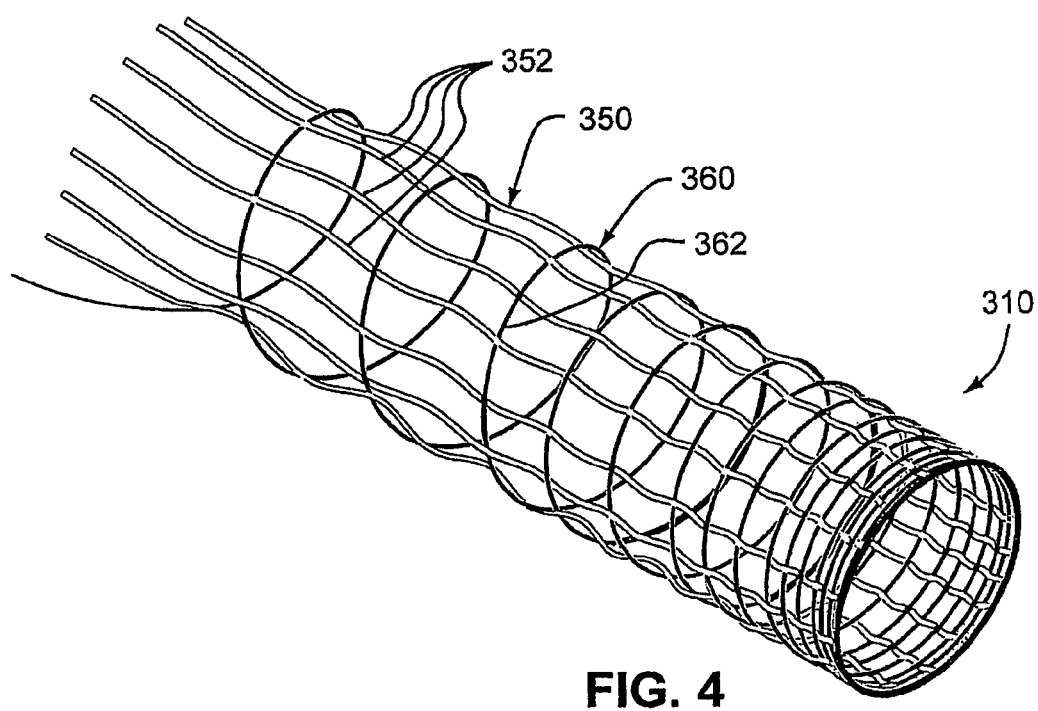
FIG. 4 is a perspective view of a textile conduit being formed by a circular weaving manufacturing process according to an embodiment of the present invention.

For example, FIG. 4 illustrates a textile conduit 310 being formed by a circular weaving manufacturing process according to an embodiment of the present invention. As illustrated, the warp 350 includes a plurality of lengthwise textile threads 352 arranged in a circle and the weft 360 includes a textile thread 362 that is woven through the warp threads 352 to make the textile conduit 310.

The textile itself could be made in a way that provides the strength to prevent kinking or obstruction. For example, the weft 360 could be made from a yarn that is semi-rigid, such as a nylon or metal, and the warp 350 would be made from another material that is flexible. This arrangement would result in a tubular structure that is flexible axially but not radially meaning that the tube would be flexible along its length but would prevent kinks and occlusions.

2.2 Gas-Permeability

In one embodiment, the wall of the textile conduit may be made from a non-porous, woven textile while in another embodiment the wall may be made from a substantially porous, woven textile and is treated such that it is substantially non-porous. A non-porous textile prevents breathing gas escaping from the conduit and the resultant pressure losses which could encroach upon the effectiveness of the respiratory therapy.

Gas or air permeability depends on the yarn size and the tightness of the weave. The surface can be treated with a resin to close the pores, or a thin film such as polyethylene may be applied over the surface. In an embodiment, a membrane such as Winstopper® by W. L. Gore & Associates, Inc. may be used. This membrane is permeable to moisture but not gas. The membrane would be applied to the inside of the conduit. If any condensation is formed in the conduit, it will pass through the membrane to the outside of the tube.

2.4 Heat Transfer

A textile conduit may be better insulated than conventional plastic conduits. To provide further insulation to the tube, additional layers of textiles (such as Thinsulate®) may be used.

In one embodiment, insulating material could be provided between each or some of the spiral or other reinforcements and a fabric or other membrane could cover the reinforcements and insulating material. The insulating material could comprise an appropriate closed cell structure, such as a resilient foam.

2.5 Weight

A textile conduit may be lighter in weight than conventional plastic conduits.

2.6 Method of Manufacture

A method for manufacturing a wall of a conduit for conveying air from a respiratory device to a patient interface is also provided. In an embodiment, the method comprises weaving a textile wall by a circular weaving technique. Such a circular weaving technique is discussed above with reference to FIG. 4.

Some of the advantages of using textiles (including woven and non-woven textiles) for a conduit are that they:

1. Have better insulating properties than plastics;
2. Are often lighter in weight than plastics; and/or
3. Have a more natural feel than plastics.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An air delivery system for treatment of obstructive sleep apnea (OSA) by providing pressurized gas to a patient's airways, the air delivery system comprising:

a patient interface configured to deliver the pressurized air to the patient's airways for OSA treatment; and
   a conduit configured to convey the pressurized air to the patient interface,
   wherein the conduit includes a wall structure that is a seamless tubular wall structure constructed from a single sheet of textile material, at least a portion of the wall structure directly conveying the pressurized air, the conduit further including a non-metallic reinforcing member structured to prevent kinking or collapsing of the wall structure, and
   wherein the will structure includes an outer surface disposed so as to be exposed directly to ambient air.

2. An air delivery system as claimed in claim 1, wherein, the reinforcing member comprises nylon.

3. An air delivery system as claimed in claim 1, wherein at least a portion of the reinforcing member is made of a semi-rigid material.

4. An air delivery system as claimed in claim 1, wherein the textile is a non-porous, woven textile.

5. An air delivery system as claimed in claim 1, wherein the textile is a porous, woven textile.

6. An air delivery system as claimed in claim 1, wherein the textile is a woven textile, manufactured by a circular weaving process.

7. An air delivery system according to claim 1, wherein the textile material comprises resin.

8. An air delivery system according to claim 1, wherein a surface of the textile material has a thin film thereon.

9. An air delivery ry system according to claim 1, wherein the wall structure includes a warp having a plurality of lengthwise textile warp threads arranged in a circle and a weft having a textile weft thread that is woven through the warp threads.

10. An a delivery systet s claimed in claim 1, wherein the wall structure rranged to be impermeable to gas.

11. An air delivery system as claimed in claim 1, wherein the reinforcing structure is disposed on the outer surface of the wall structure.

12. An air delivery system to provide pressurized gas to a patient's airways, comprising:
    a positive airway pressure device configured for treatment of obstructive sleep apnea (OSA);
    a conduit configured to convey the pressurized gas from the positive airway pressure device to a patient interface, wherein the conduit includes a seamless tubular wall structure constructed from a single sheet of textile material so that the seamless tubular wall structure directly conveys the pressurized gas,
    wherein a reinforcing member is disposed on an outer surface of the wall structure, the reinforcing member being structured to prevent kinking or collapsing of the wall structure, wherein the outer surface is disposed so as to be directly exposed to ambient air.

13. An air delivery system accorditut to claim 12, wherein the reinforcing member includes a spiral or helical shape.

14. An air delivery system according to claim 12, wherein the reinforcing member is constructed of plastic.

15. An air delivery system according to claim 12, wherein the textile material is a woven textile.

16. An air delivery system according to claim 12, wherein the textile material comprises resin.

17. An air delivery system according to claim 12, wherein a surface of the textile material has a thin film thereon.

18. An air delivery system according to claim 9, wherein the warp is constructed from flexible threads.

19. An air delivery system according to claim 12, wherein the wall structure includes a warp having a plurality of lengthwise textile warp threads arranged in a circle and a weft having a textile weft thread that is woven through the warp threads.

20. An adelivery system according to 19, wherein the warp is constructed from flexible threads.

21. An air delivery system ae rdir g to clam 12, wherein the seamless tubular wall structure is arranged to be impermeable to gas.

\* \* \* \* \*

UNITED STATES PATENT AND TRADEMARK OFFICE
CERTIFICATE OF CORRECTION

PATENT NO.        : 9,566,408 B2
APPLICATION NO.   : 12/225417
DATED             : February 14, 2017
INVENTOR(S)       : Henry It is certified that error appears in the above-identified patent and that said Letters Patent is hereby corrected as shown below:

In the Claims

Claim 1, at Column 4, Line 66, "wherein the will structure includes an outer surface disposed" should read ---wherein the wall structure includes an outer surface disposed---.

Claim 2, at Column 5, Line 1, "An air delivery system as claimed in claim 1, wherein," should read ---An air delivery system as claimed in claim 1, wherein---.

Claim 9, at Column 5, Line 17, "An air delivery ry system according to claim 1, wherein" should read ---An air delivery system according to claim 1, wherein---.

Claim 10, at Column 5, Line 23, "An a delivery systet s claimed in claim 1, wherein the wall structure rranged to be" should read ---An air delivery system as claimed in claim 1, wherein the wall structure is arranged to be---.

Claim 13, at Column 6, Line 10, "An air delivery system accorditut to claim 12, wherein" should read ---An air delivery system according to claim 12, wherein---.

Claim 20, at Column 6, Line 27, "An adelivery system according to 19, wherein the" should read ---An air delivery system according to claim 19, wherein the---.

Claim 21, at Column 6, Line 29, "An air delivery system ae rdir g to claim 12, wherein" should read ---An air delivery system as claimed in claim 12, wherein---.

Signed and Sealed this
Eleventh Day of April, 2017

Michelle K. Lee
*Director of the United States Patent and Trademark Office*